United States Patent [19]

Stein

[11] Patent Number: 5,040,199
[45] Date of Patent: * Aug. 13, 1991

[54] APPARATUS AND METHOD FOR ANALYSIS USING X-RAYS

[75] Inventor: Jay A. Stein, Framingham, Mass.

[73] Assignee: Hologic, Inc., Waltham, Mass.

[*] Notice: The portion of the term of this patent subsequent to Mar. 7, 2006 has been disclaimed.

[21] Appl. No.: 319,994

[22] Filed: Mar. 7, 1989

Related U.S. Application Data

[63] Continuation-in-part of Ser. No. 78,419, Jul. 27, 1987, Pat. No. 4,811,373, which is a continuation-in-part of Ser. No. 885,098, Jul. 14, 1986.

[51] Int. Cl.$^5$ ............................................. G01B 15/02
[52] U.S. Cl. ...................................... 378/56; 378/54; 378/146; 378/207
[58] Field of Search .................................... 378/51-56, 378/110-112, 207, 62, 146, 204, 4, 16

[56] References Cited

U.S. PATENT DOCUMENTS

| Re. 28,544 | 9/1975 | Stein et al. |
|---|---|---|
| 3,848,130 | 11/1974 | Macovski |
| 3,944,830 | 3/1976 | Dissing |
| 3,996,471 | 12/1976 | Fletcher et al. |
| 4,029,963 | 6/1977 | Alvarez et al. |
| 4,445,226 | 4/1984 | Brody ................................ 378/99 |
| 4,639,943 | 1/1987 | Heinze et al. |
| 4,641,331 | 3/1987 | Makino et al. |
| 4,811,373 | 3/1989 | Stein ................................. 378/207 |

OTHER PUBLICATIONS

Jay A. Stein, Ph.D., "X-Ray Imaging with a Scanning Beam", Radiology, vol. 117, No. 3, pp. 713-716, Dec. 1975.
Sartoris et al., Bone Mineral Density in the Femoral Neck, American Journal of Roentgenology, vol. 144, p. 605 (1985).
Gustafsson et al., X-Ray Spectrophotometry for Bone--Mineral Determinations, Medical and Biomedical Engineering, p. 113 (Jan. 1974).
Cann, A Clinicians Guide to the Use of Bone Mass Measurements, University of California, pp. 1-36 (unpublished), no date.
Wahner et al., Non-Invasive Bone Mineral Measurements, Seminars in Nuclear Medicine, vol. XIII, No. 3, p. 282, Jul. 1983.
Dunn et al., Measurement of Bone Mineral Content in Human Vertebrae and Hip by Dual Proton Absorptiometry, Radiology, vol. 136, No. 2, p. 485 (Aug. 1980).
The "Norland Dichromatic Bone Densitometer" pamphlet, no date.
Lehmann et al., Generalized Image Combinations in Dual KVE Digital Radiography, Medical Physics, vol. 8, No. 5, p. 659, Sep./Oct. 1981.

Primary Examiner—Edward P. Westin
Assistant Examiner—David P. Porta
Attorney, Agent, or Firm—Fish & Richardson

[57] ABSTRACT

An x-ray analysis apparatus with an x-ray tube which generates an x-ray beam to expose an object to be analyzed. The apparatus inserts into and removes from the x-ray beam a piece of reference material such that regions of the object are exposed both to the x-ray beam and the x-ray beam obstructed by the reference material. A detector detects x-rays passing through the object and produces an indication of the object based upon the signals produced by the exposure to the x-ray beam and upon the signals produced by the exposure to the x-ray beam obstructed by the reference material.

40 Claims, 6 Drawing Sheets

APPARATUS AND METHOD FOR ANALYSIS USING X-RAYS

This application is a continuation-in-part of Parent U.S. patent application Ser. No. 078,419 filed July 27, 1987, now issued as U.S. Pat. No. 4,811,373, which is a continuation-in-part of U.S. patent application Ser. No. 885,098, filed July 14, 1986, both of which are herein incorporated by reference.

The invention concerns determining the nature of a body of interest using an x-ray source.

The parent patent application illustrates techniques of the invention applied to a bone densitometer for measuring the amount and distribution of bone in the human body. The particular embodiment shown, which employs a raster scan of a pencil beam of dual energy x-rays, is especially useful for measuring bone density of the spine or similar region.

Other embodiments of the basic techniques are presented in this patent. These, which are important in themselves, also illustrate the generality of the broader aspects of the original invention.

The invention can lead to improvement in measurement time, resolution, accuracy, precision and minimization of radiation dose in analyses of objects using x-rays.

In the application of the invention to dual energy analyses, the invention takes advantage of the high photon intensity provided by x-ray sources by overcoming certain problems associated with using x-rays. Although x-ray sources are more intense than radiosotopic sources such as used in bone densitometry, they are also less stable because they vary (drift) with changes in the voltage and current supplied to them. In addition, x-ray tubes produce photons that have a broad range of energies whereas radiosotopic sources typically produce photons with only a few energies.

SUMMARY OF THE INVENTION

These and numerous other problems are met by a system, according to the invention, that provides reference data over all regions of the area of the body being examined. This may advantageously be done even on a pixel-by-pixel basis, or a close approximation to it.

According to one aspect of the invention, an x-ray analysis apparatus is provided comprising an x-ray tube means and associated power supply which generates an x-ray beam, means to expose to the x-ray beam an object to be analyzed, means to insert into and remove from the x-ray beam a piece of reference material of predetermined properties such that all regions of the object are exposed both to the x-ray beam and to the beam obstructed by the reference material, detector means arranged on the opposite side of the object to detect x-rays and produce signals corresponding to the amount of x-rays transmitted through the object, and signal processing means responsive to signals from the detector means to produce an indication of the nature of the object based upon the signals produced by the exposure to the x-ray beam and the signals produced by the exposure to the x-ray beam obstructed by the reference material of predetermined properties.

Preferred embodiments of this aspect of the invention have the following features.

The signal processing means is responsive to distinguish, from the set of signals produced by the x-ray beam, a subset of signals which corresponds to regions of the object having a predetermined property.

The means to expose the regions to the x-ray beam is a scanning means constructed to scan the beam in a pattern over the object and the means to insert the piece of reference material is constructed and arranged to cause any point of the object exposed to the unobstructed beam to lie substantially adjacent to a point exposed to the beam while obstructed by the reference material.

The means to insert and remove the reference material is constructed to act on lines of scan distributed throughout the pattern of the scan.

The x-ray tube means is constructed to produce a fan beam.

The apparatus is adapted to effectively examine the object at more than one level of x-ray energy.

The power supply comprises means for applying alternate high and low voltage levels to the x-ray tube and the means to insert the reference material into the x-ray beam comprises a rotating carrier which carries the piece into and out of the x-ray beam.

Another aspect of the invention is an apparatus having a detector responsive to the absorption characteristics of an object exposed to a radiation beam of at least two different energies form an x-ray source, the apparatus including a reference system which is capable of interposing into said radiation beam, substantially over the extent of the exposure, a material of known absorption characteristics, and signal processing means capable of using the known absorption characteristics of the reference system and the absorption characteristics of the object measured by the detector both with and without the presence of the reference material in the beam to determine a characteristic of the object.

According to another aspect of the invention, in the case of bone densitometers, an important feature of the invention is a calibration technique which determines the location of bone and then calibrates the measurements on the basis of x-ray data produced from non-bone areas that lie close to the location of bone. Such calibration not only accomodates drift of the x-ray source but also other variations encountered, such as, detector drift, variation in body thickness from patient to patient, and also effects caused by hardening of the x-ray spectrum as the beam passes through the patient.

According to another aspect of the invention, a bone densitometer is provided for measuring density of bone-like material in a patient who is held in fixed position, comprising an x-ray tube means having a power supply, detector means arranged on the opposite side of the patient to detect x-rays attenuated by the patient, means to effectively expose portions of the patient having bone and adjacent portions having only flesh (non-bone body substance), means for causing the beam to pass through a bone-like calibration material in the course of the exposure, and signal processing means responsive to the output of the detector means to provide a representation of bone density of the patient (e.g., an x-ray film-like picture of the patient, showing bone density distribution or calculated values representing bone density of the patient), the signal processing means adapted to respond to data based upon x-rays attenuated by the calibration material in regions having only flesh to calibrate the output of the detector means, thereby enabling the accommodation of drift in the x-ray tube, differences in patient thickness and other system variations.

According to another aspect of the invention, a bone densitometer, e.g., having the features described above, further comprises a fan beam collimator arranged to form and direct a fan beam of x-rays through the patient, and the detector means, on the opposite side of the patient, is aligned with the collimator; the x-ray tube, fan beam collimator and detector means are adapted to be driven in unison in scan relative to the patient, and rotating means are adapted to cause the beam to pass through bone-like calibration means. According to this aspect of the invention, the signal processing means is not limited to responding to data based upon x-rays attenuated by the calibration material in regions having only flesh to calibrate the output of the detector means.

According to another aspect of the invention, a bone densitometer incorporates features of both of the above-described bone densitometer aspects of this invention.

A further aspect of the invention utilizes a fan beam made of a series of pencil beams in order to reduce the radiation dosage to a patient.

In a preferred embodiment of these aspects of the invention, the power supply of the bone densitometer is adapted to apply alternate high and low voltage levels to the x-ray tube; control means for the frequency of the voltage is related to the speed at which the x-ray tube, collimator and detector means are driven in scan motion and the beam thickness produced by the collimator to apply alternating high and low voltage levels to the x-ray tube at a frequency sufficiently high that at least one pair of high and low level exposures occurs during the short time period during which the fan beam traverses a distance equal to about one beam thickness, preferably the bone densitometer being adapted to produce pairs of high and low voltage pulses at a rate of the order of sixty per second, the x-ray tube, collimator and detector means being driven along the scan at a rate of the order of one inch per second and the collimator produces a fan beam of between about one and three millimeters in thickness; the x-ray beam passes through the bone-like calibration material at least twice per every four scan positions for a period about equal to or less than the time during which one line of resolution is traversed, preferably the x-ray beam passes through the bone-like calibration material for the duration of every other high and low voltage pulse pair; the detector means comprises an integrating detector controlled to integrate the detected signal repeatedly over time periods less than or about equal to the time required to advance the x-ray scan pattern by one line of resolution, preferably an analog to digital converter being provided to convert each integrated value from each detector to a digital signal and a digital computer means is provided for producing the representation of bone density of the patient by processing the stream of the digital signals.

According to still another aspect of the invention, a bone densitometer incorporates an x-ray image intensifier tube and a cone of radiation rather than a scanning fan-beam. One image at each energy without an absorber in the beam and one image at each energy with a bone-like absorber in the beam is taken of the patient.

The present invention makes it possible to perform bone density measurements and other analyses more rapidly and with better resolution and accuracy than prior devices. Because it does not use radioisotopic sources, the user does not need to handle and replace radioactive materials which are dangerous and are strictly controlled by federal licensing regulations.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

FIG. 1a is a diagrammatic illustration of the preferred embodiment utilizing a fan beam, while

FIG. 2 is a plan view of the calibration disc employed in the preferred embodiment with a fan beam, while

DESCRIPTION OF ILLUSTRATIVE EMBODIMENTS

Figure 1:
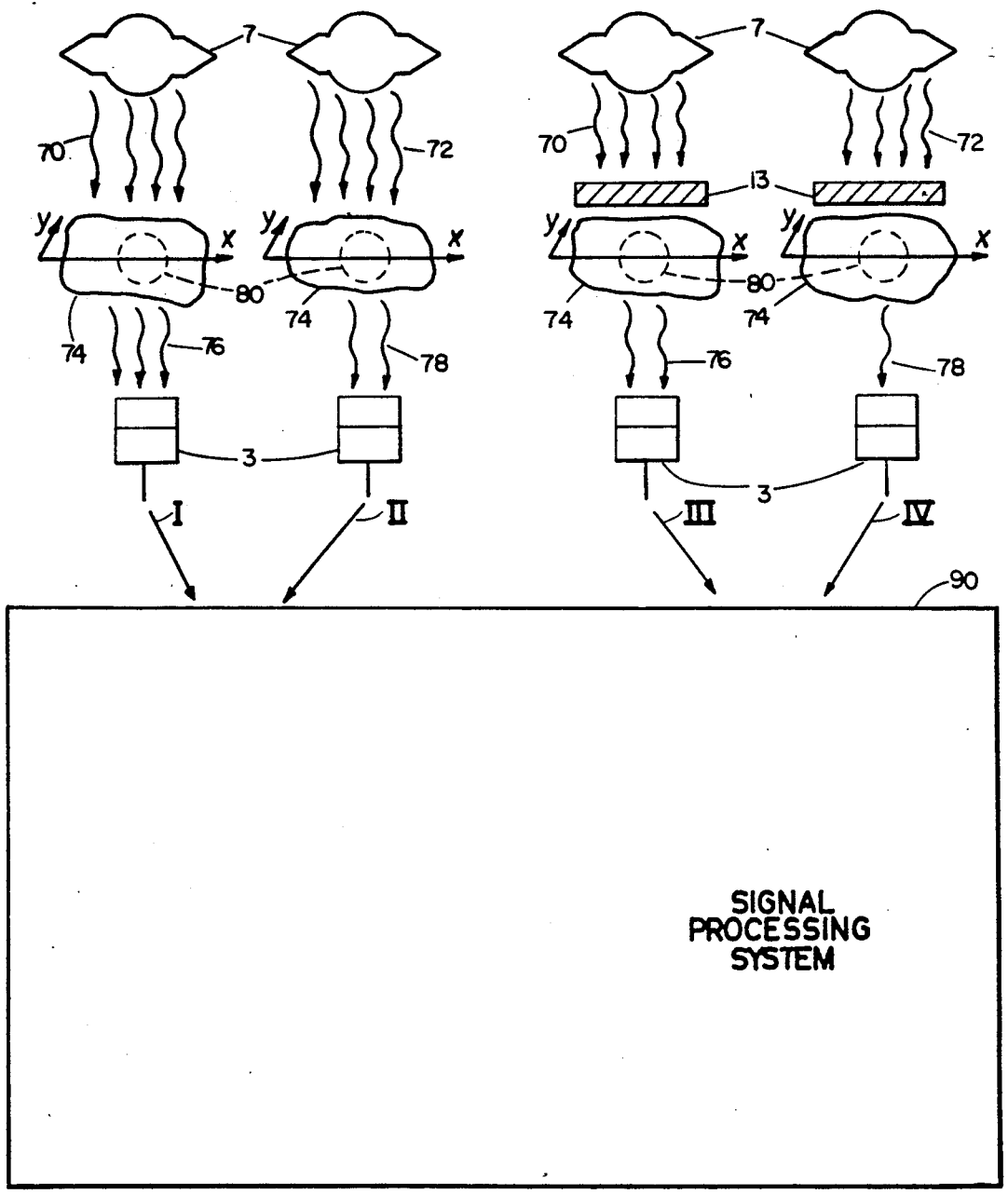
FIG. 1 is a block diagram illustrating basic techniques according to the invention.

FIG. 1 represents, schematically, broad aspects of the reference system of the invention of the parent patent application.

On the left side of the figure it is indicated by the X, Y coordinates that object 74 containing a subject of interest, 80, is exposed to x-rays 70 from source 7 over the area of interest and the transmitted rays 76 are detected at 3 to produce Image I while to the right in the figure the area of the object is exposed with x-rays 70 that also pass through reference material 13 of predetermined absorption characteristics, to produce Image III.

A signal processing system 90 can receive signals representing these images taken with and without the reference material, and use both to make a determination of characteristic of the object. The nature of the particular use can vary widely, e.g. to perform a pixel by pixel calibration of the system to compensate for drift of the source or detector, to compensate for varying thickness of extraneous material, or to make a determination based on specific absorption qualities of the reference material being employed.

In the particular system here represented, the x-ray tube 7 produces x-rays of two energies; high-energy 70 and low-energy 72. In actuality a broad spectrum of x-rays may be produced and only two energy regions of interest allowed to strike the object 74, or allowed to be detected.

Those x-rays of both energies which pass through the object 74, respectively rays 76 and 78, strike detector 3 in the manner that a set of signals representing an image of the object is produced at each beam energy. The object 74 absorbs more of one of the x-ray energies and reduces its intensity (the number of x-rays per unit area), more strongly than the other. The amount of such attentuation of the x-rays beam is determined by the attenuation coefficient ($\mu$) of the object and this attentuation coefficient is strongly dependent on the energy of the x-rays being attentuated.

By using the dual-energy beam method along with the use of the reference material in and out of the beam, effectively four different images are formed: two with high energy, Image I without and Image III with the reference material 13, and two images with low energy, Image II without and Image IV with the reference material.

With such data many determinations are possible by suitable signal processing, of which areal density, location of bone, and more accurate digital representation of x-ray images are only a few examples.

The systems now to be described also are embodiments of the two aspects of the invention illustrated in FIG. 1.

Figure 1A:
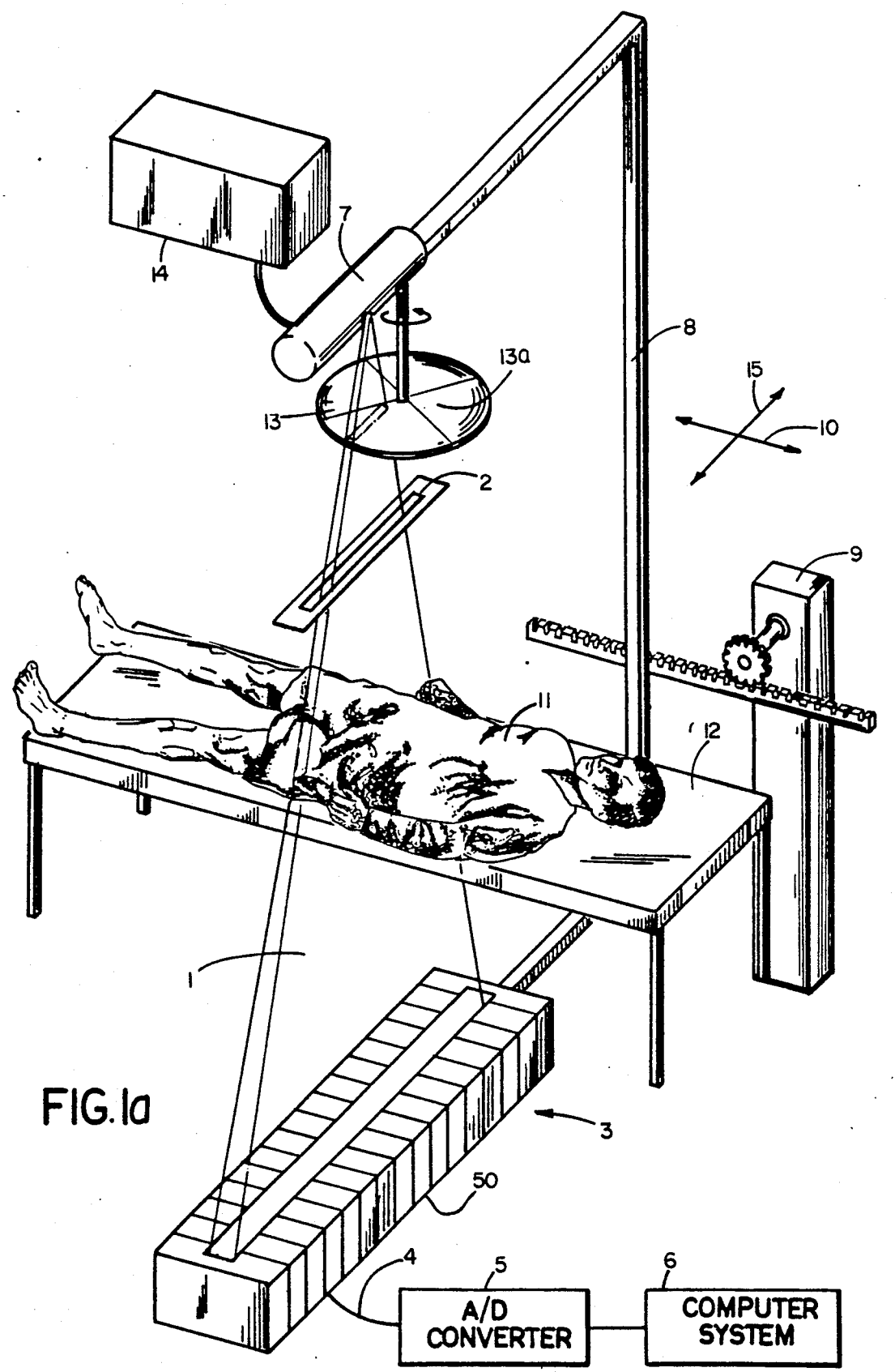

An embodiment employing a fan beam is shown in FIG. 1a. A source of x-ray radiation 7 energized by a high voltage power supply 14 produces x-rays which pass through sectors 13a of a calibration wheel 13 carrying reference material chosen for purposes of calibration and which are formed into a fan beam 1 by a slit collimator 2. The radiation is transmitted through the patient 11 and the support table 12 to impinge on an array of x-ray detectors 3. The array of detectors 3 typically consists of a linear array of 50 to 100 silicon photodiodes 50 which are covered with either an x-ray scintillation screen or an x-ray scintillation crystal. The screen or crystal produces light when struck by x-rays and the light is detected by the photodiodes 50 of the detectors 3 which produce electrical signals 4. These signals 4 are the input signals for an analog to digital (A/D) converter 5. The digital output of the A/D converter is stored in a computer system 6 for further processing. The x-ray source 7, calibration wheel 13, slit collimator 2 and detector array 3 are rigidly connected by mechanical means 8 so that they may be translated in a rigid fashion together by translation mechanism 9. The detector array 3, x-ray source 7, calibration wheel 13 and slit collimator 2 are moved by the translation mechanism 9 in the direction of arrow 10 along the patient 11. Alternatively, the system may be designed so that the mechanism 9 can be made to cause the direction of translation to be across (arrow 15) patient 11. Such an arrangement would also require the changing of the orientation of the slit collimator 2 and the detector array 3 by reorienting them 90° about the source-detector axis.

Also, other means besides the calibration wheel 13 can be used to insert and remove the calibration material. For example, a solenoid could be used to periodically insert the calibration material into and remove the calibration material from the beam.

Figure 2:
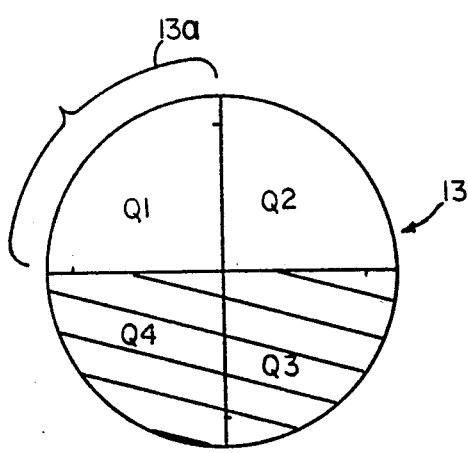

Considering the components in detail, the x-ray source 7 is typically an x-ray tube having a cathode and an anode. Electrons are accelerated by the voltage between the anode and cathode and strike the anode. The anode is typically made of tungsten and the collision of electrons with the anode results in the emission of x-radiation from the point of collision with the anode, called the focal spot. Referring now also to FIG. 2, the x-ray beam then passes through the calibration wheel 13 consisting of a number of sectors 13a. Alternatively, the calibration wheel 13 can be located between the slit collimator 2 and the patient 11. In one embodiment there are four sectors 13a, labeled Q1 through Q4. Two sectors, for example Q3 and Q4 contain a bone-like calibration material of uniform thickness, and accordingly with a known absorption characteristic. As the wheel 13 rotates, the x-ray beam passes through each of the quadrants 13a of the wheel 13 sequentially. Although the discussion to follow will be premised on a four sector calibration wheel 13, a larger number of segments can be used with certain advantages. For example, a calibration wheel 13 may have six segments with the additional segments having a second known absorption characteristic. These additional segments allow additional calibration points to be generated. The more available calibration points, the better defined the absorption curve for each locality being examined. In this way, one would have a better description of the curve representing the response of the instrument to a range of bone areal densities (gms./sq. in.) that may appear at that locality. The calibration material may also have multiple known thicknesses so long as the signal processing system has provision for being able to associate each signal received with the thickness employed.

After passing through the wheel 13, the x-rays from the anode are interrupted by the slit collimator 2 and turned into a fan beam 1. The slit collimator 2 is made of an x-ray opaque material such as lead or tungsten in which a rectangular slot has been machined. Thus the radiation passing through the slot in the collimator 2 forms a fan shape in space. Preferrably, as shown, the slit collimator is aligned to correspond with a radius of the wheel, so that the quadrant affects the fan beam uniformly during the full time of its rotation past the slit.

The calibration wheel 13 is used in conjunction with a dual-energy x-ray technique wherein the x-ray exposure of the patient can be viewed as taking place at two different energies There are several methods for accomplishing this.

Figure 3:
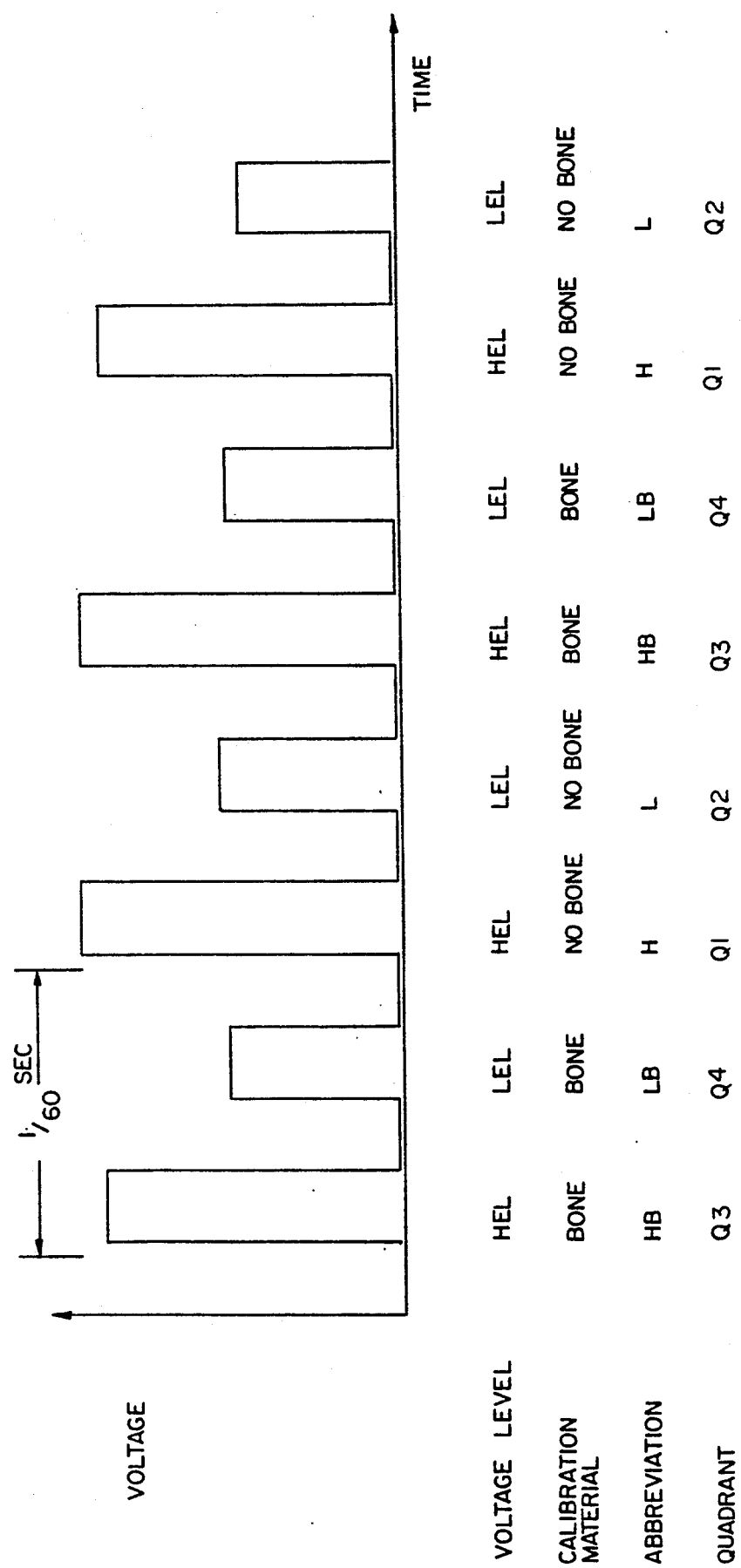
FIG. 3 is an illustration showing the time relationship between the voltage levels produced during the high energy level (HEL) and low energy level (LEL) phases of energization of the x-ray tube and the motion of the synchronized calibration wheel having "bone" and "no bone" quadrants.

In one embodiment, the x-ray source 7 is an x-ray tube driven by power supply 14 which operates in a pulsed, two voltage level manner. By operating the tube at alternately high- and low- kilovoltages, the x-ray radiation produced consists of an alternating series of predominately high energy and lower energy x-rays. For example, in one embodiment the high energy pulses are produced at 150 kilovolts and the low energy pulses at 75 kilovolts. The tube current in this case is typically kept constant, between about 5 and 500 hundred milliamps. The pulses so generated are spaced such that the time between the start of one pulse and the start of an adjacent pulse of different energy is 1/120 of a second. FIG. 3 depicts the time series of high energy (HEL) and low energy (LEL) pulses. Note that the time between adjacent pulses of the same energy is 1/60 sec.

Figure 4:
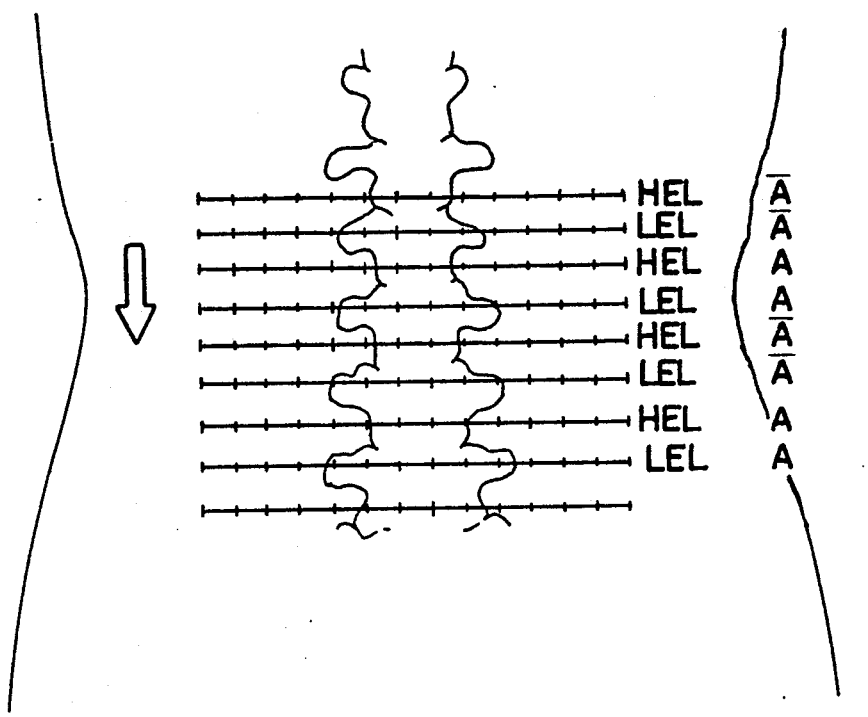
FIG. 4 represents a patient's spine with superposed scan pattern.
Figure 2A:
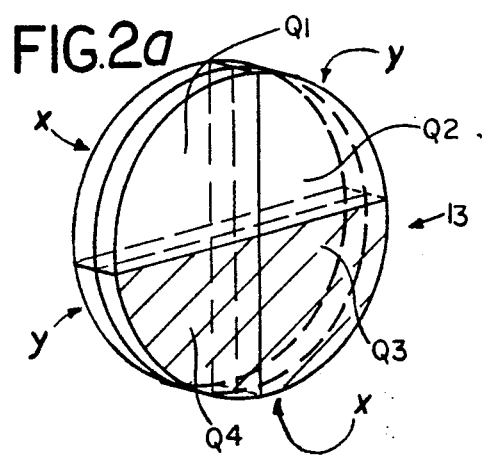
FIG. 2a illustrates an alternative which combines filtering material with the calibration wheel.
Figure 6:
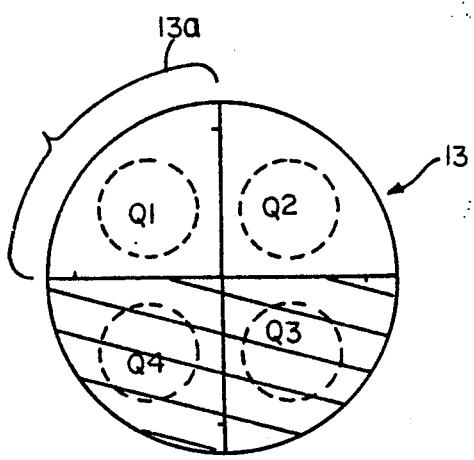
FIG. 6 is a plan view of the calibration disc employed in the preferred embodiment with a cone beam.

This dual energy beam is used in conjuction with the calibration wheel 13 in the following manner. The first quadrant of the wheel 13 labled Q1 corresponds to a high energy pulse. The second quadrant labeled Q2 corresponds to low energy pulse. Q3 corresponds again to a high energy pulse but with known calibration material in the path of the beam, while Q4 corresponds to a low energy pulse but also with known calibration material in the path of the beam. The pulses and the calibration wheel sectors 13a are synchronized such that there are sequential lines in the scan of the patient 11 occuring with high energy x-rays, low energy x-rays, high energy x-rays with known attentuation and low energy x-rays with known attenuation. As shown in FIG. 4 those without attenuation are denoted by "A" and those with attenuation are denoted by "A". The lines are actually much closer than shown in FIG. 4. There are typically at least four lines such as shown in FIG. 4 every 1 or 2 mm of scan distance. Referring to FIG. 2a it is possible to include different filtering materials in the quadrants that also correspond to the high and low energy pulse to shape the energy spectrum of the x-ray beams.

Indeed a second embodiment forms the dual energy beam by using a filtering techniques instead of variation of voltage on the x-ray source. In this embodiment, the x-ray tube 7 of FIG. 2 is operated at a constant voltage. Referring to FIG. 2a, different, selected materials X, Y are provided in the wheel 13 to filter the x-ray beam differently and alternately so that during passage of one sector 13a of the wheel 13, the emerging beam contains a concentration of high-energy photons, while during the next sector the emerging beam has a concentration of low-energy photons.

This is possible since a typical source generates a spectrum of x-rays and different filter materials can be selected to allow the preferential transmission through the material of either more of the high-energy or more of the low-energy x-rays. In order to allow more of the low energy x-rays to pass through, K-edge filtering can be used. K-edge filtering makes use of the property of materials called the K-absorption edge. The K-absorption edge absorbs high energy photons preferentially over photons that have energy below this K-edge. Some rare earth materials such as gadolinium or samarium have a K-edge in the neighborhood of 40 to 50 kilovolts. This is in the region of separation between the high and low energy photons which is of use in bone measurement applications. K-edge filtering is well known to the art.

Figure 1C:
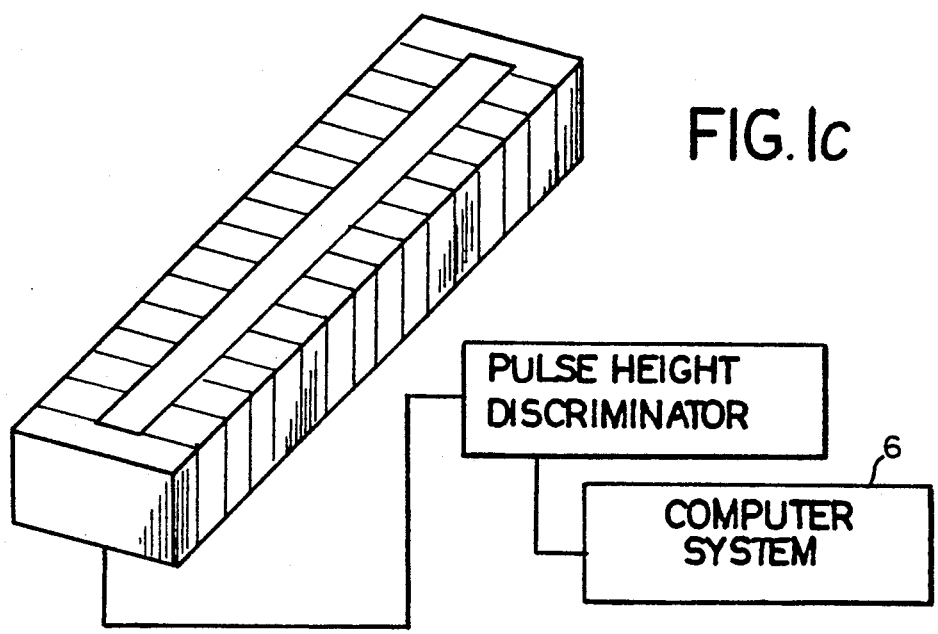
FIG. 1b illustrates an alternative using a sandwich detector and FIG. 1c illustrates an alternative using pulse height analysis.
Figure 1B:
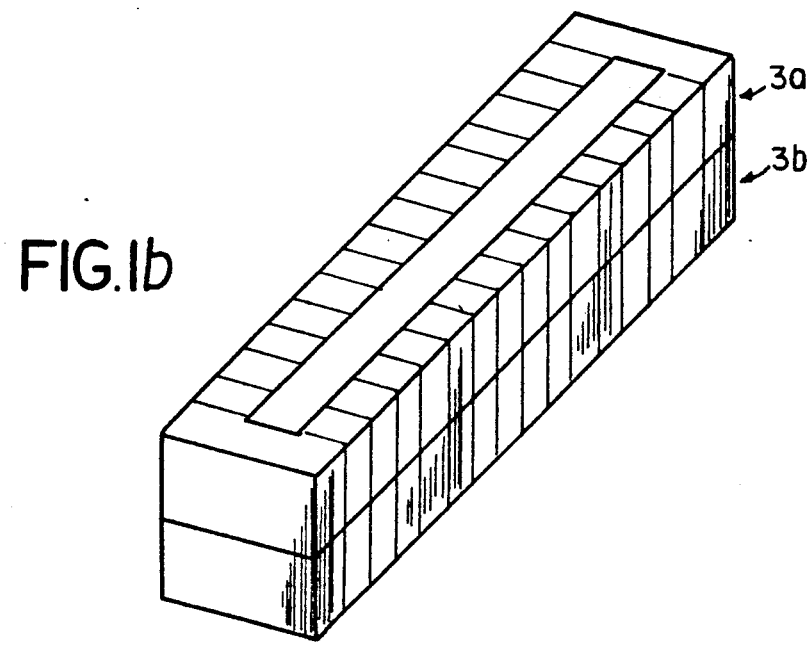

Another embodiment of the invention obtains dual-energy exposures with an unmodulated beam by using a sandwich detector, FIG. 1b, in which each detector element consists of a sandwich of two detectors 3a and 3b. Detector 3a which first receives the radiation tends to absorb the low-energy x-rays, while detector 3b behind the first detector tends to absorb the high-energy x-rays which penetrate the first detector. Such a sandwich detector using different scintillation materials is well known in the art.

Another embodiment of the invention, FIG. 1c,, performs the dual energy exposure technique employing pulse height analysis. In this embodiment the x-ray tube is operated at a single kilovoltage and a set of pulse height discriminators, one associated with each x-ray detector operates so as to count separately the number of photons that are at a defined high energy or at a defined low energy. In pulse height analysis, the detectors may be larger than those which are used in other dual energy techniques so it is not possible to locate the detector elements close together. In such cases it is prudent to modify the fan beam of x-rays striking the patent.

Consider a case using pulse height analysis where the number of detectors is not large, for example ten, and wherein the center lines of the detectors are separated by a significant distance, for example one inch center to center. Then it is prudent to collimate the fan beam into a linear series of separate pencil beams. In this example, ten beams are produced and are arranged so that each beam strikes a separate detector. The radiation between the detectors is blocked and therefore does not go through the patient, eliminating unnecessary exposure.

In this embodiment, the pencil-fan beam is then partially raster scanned, following techniques described in the parent patent application, to enable all parts of the patient to be covered by this fan array of pencil beams. The fan beam is moved at least far enough laterally, which in this example would be about 1 inch, to cause the individual pencil beams making up the fan to pass across all regions of the patient at each line of scan. In this embodiment the total time to complete a scan of the patient is less than the time required with a single pencil beam, but greater than the time required for a scan using a full fan beam. A benefit from such a system is the reduced cost of the smaller number of detector elements.

Figure 5:
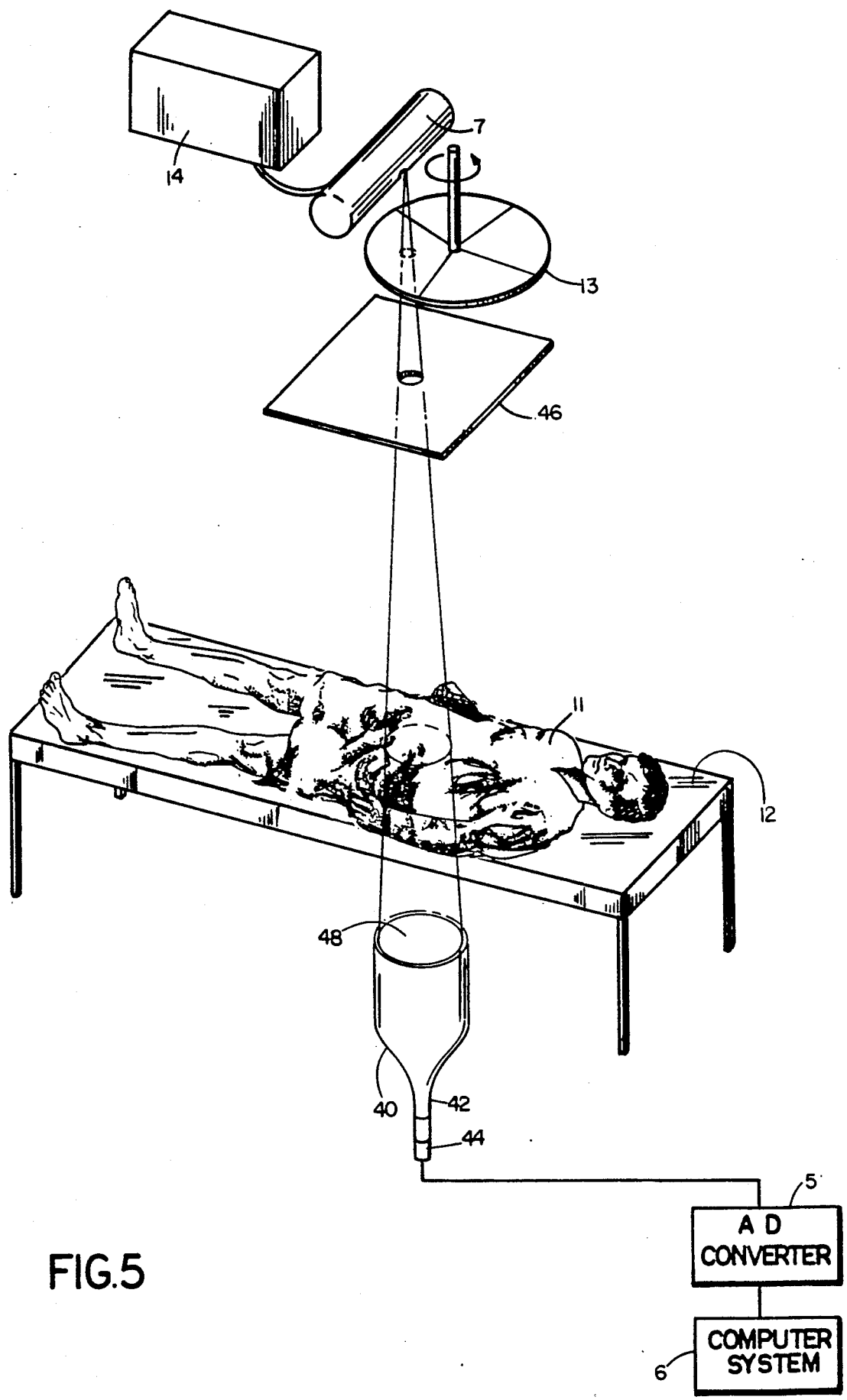
FIG. 5. is a diagrammatic illustration of another embodiment utilizing a cone beam.

In addition to the fan beam having a continuous distribution of x-rays and a fan beam formed by an array of pencil beams, which have just been discussed, still another embodiment of the invention uses a cone of radiation rather than fan or pencil beam. Referring to FIG. 5, the x-ray tube 7 again emits a broad beam of radiation which, after passing through the calibration wheel 13 passes through a cone collimator 46. The radiation which passes through the patient 11 and the support table 12, impinges on a broad beam x-ray detector 40. This detector 40, is preferentially an x-ray image intensifier. This device converts the x-ray image formed on the face 48 of the intensifier generally into a much smaller optical image on the output face plate 42. This output face plate 42 is viewed by a television camera 44 which produces an output which is then digitized by an A/D converter 5 and the digitized values are stored in the computer system 6 for further processing.

Figure 7:
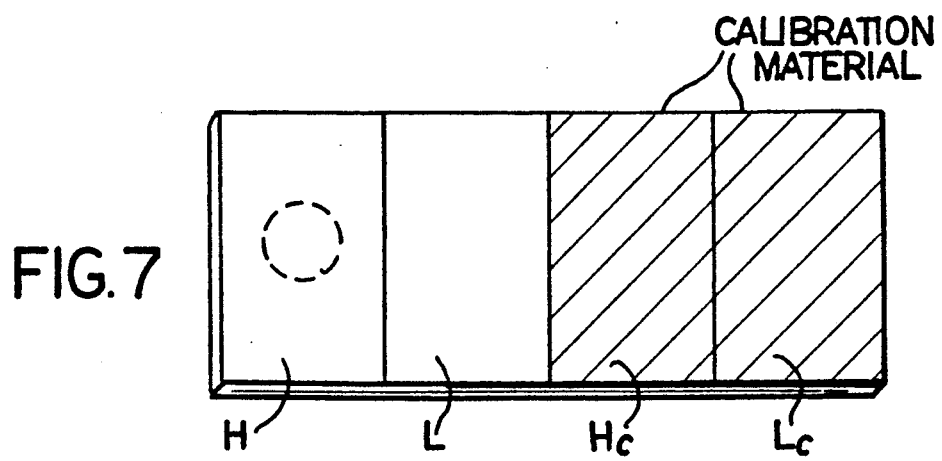
FIG. 7 is a plan view of a calibration device in linear form for use with a cone beam.

In this system only four pulses of x-rays are required, two high energy and two low energy. Again the calibration wheel 13 can be employed, but in this embodiment only one rotation can be required. The result is that four separate images are formed; two each with high and low energy x-rays and two each with and without the bone calibration material. Because only four images are taken, and each of the four calibration conditions is used only once, it may be preferred to place the calibration material on a slide as shown in FIG. 7 instead of the wheel shown in earlier embodiments. The advantage of the cone technique is its speed. It is possible to acquire all the required bone density data for a patient in about a second or less.

In all of these embodiments, all measurements of patient bone density are referenced to and corrected by measurements made with a known amount of bonelike material in the beam. This makes it possible to calculate a bone mineral value in the patient which is not dependent on the stability of the x-ray tube, the detectors, the patient thickness or the x-ray spectrum. Thus the variation in the measurement which depend upon those variables is removed.

It is possible to use this invention to create a whole body bone densitometer. In a whole body bone densitometer, the variation in density of the various bones in the body requires that the calibration take place with a number of bone-like calibration thicknesses rather than the single thickness just described. This is due to the instrument's not necessarily being linear over a large density range. To correct for this, for example, with three thickness of bone-like material (that is, in an eight sector wheel) the calibration points can be best fit to a straight line or higher order curve.

Once the image has been digitized and stored, the computer processes the data as described in the parent application. The processing calculates a value for the bone mineral content in a segment of the patient's body using a known method. Then the calculated values are corrected or calibrated using measurements obtained when the bone-like calibration material was inserted in the beam.

The reference system as well as the dual photon exposure techniques of the present invention will be found useful for other determinations as well as density measurement of known materials in a body of interest. An example is determination of whether a substance of known specific density or absorption property is present, regardless of amount. This will be useful e.g. in medical diagnosis as well as in assisting with baggage inspection at airports and the like. The disclosure of a U.S. patent application entitled X-ray Baggage Inspection and the Like, also a Continuation-in-Part of U.S. Ser. No. 078,419, being filed simultaneously with this application, is herein incorporated by reference.

Having described a number of embodiments, those skilled in the art will realize many variations are possible which will still be within the scope and spirit of the claimed invention. Therefore, it is the intention to limit the invention only as indicated by the scope of the claims.

What is claimed is:

1. An x-ray analysis apparatus for determining the content of a material of interest within an object comprising an x-ray tube means and associated power supply which generates an x-ray beam, means to expose to the x-ray beam an object to be analyzed, means to insert into and remove from the x-ray beam a piece of reference material in the manner that all regions of the object are exposed both to the x-ray beam and to the x-ray beam obstructed by the reference material, said reference material having x-ray absorption properties substantially corresponding to those of said material of interest, detector means arranged on the opposite side of the object to detect x-rays and produce signals corresponding to the amount of x-rays transmitted through the object, and signal processing means responsive to signals from the detector means to produce an indication of the content of said material of interest in the object based upon the signals produced by the exposure to the x-ray beam and the signals produced by the exposure to the x-ray beam obstructed by the reference material.

2. The x-ray analysis apparatus of claim 1 wherein said signal processing means is responsive to distinguish, from the set of signals produced by the x-ray beam, a subset of signals which corresponds to regions of the object having a predetermined property.

3. The x-ray analysis apparatus of claim 1 wherein the means to expose the regions to the x-ray beam is a scanning means constructed to scan the beam in a pattern over the object and the means to insert the piece of reference material is constructed and arranged to cause any point of the object exposed to the unobstructed beam to lie substantially adjacent to a point exposed to the beam while obstructed by the reference material.

4. The apparatus of claim 3 in which said means to insert and remove the reference material is constructed to act on lines of scan distributed throughout the pattern of the scan.

5. The apparatus of claim 3 in which said x-ray tube means is constructed to produce a fan beam.

6. The apparatus of any of the claim 1 in which said means to insert and remove the reference material comprises a rotating carrier constructed to repeatedly carry the piece of material into and out of the beam during the scan.

7. The apparatus of any of the claims 1, 5 or 6 adapted to effectively examine the object at more than one level of x-ray energy, said means to insert into and remove reference material adapted to act upon beams of each level of x-ray energy.

8. The apparatus of claim 1 wherein said power supply comprises means for applying alternate high and low voltage levels to said x-ray tube.

9. An apparatus responsive to the absorption characteristics of an object exposed to a radiation beam of at least two different energies from an x-ray source, the apparatus including an x-ray source, a detector, and a reference system which is capable of interposing into said radiation beam substantially over the extent of the exposed area of the object a material of known absorption characteristics in a manner to produce four sets of absorption data independent of the object being examined, namely high energy without reference material interposed, high energy with reference material interposed, low energy without reference material interposed and low energy with reference material interposed, and signal processing means responsive to said four sets of data and capable of using the known absorption characteristics of said reference system and the absorption characteristics of the object as represented by x-rays reaching the detector, both with and without the presence of the reference material in the beam, to determine a characteristic of the object.

10. The apparatus of claim 9 wherein said object is a patient, said reference material comprises a piece of bone-like calibration material of predetermined properties, and said apparatus is in the form of a bone densitometer for measuring bone content in the patient, said x-ray source comprising an x-ray tube means and associated power supply which generates an x-ray beam;

means to expose the x-ray beam to the patient, means to repeatedly insert into and remove from the x-ray beam said piece of bone-like calibration material such that regions of the patient are exposed both to the x-ray beam and to the beam obstructed by said bone-like calibration material;

said detector arranged on the opposite side of the patient to detect x-rays and produce signals corresponding to the amount of x-rays transmitted through the patient, and said signal processing means responsive to signals from the detector to produce a measurement of bone content based upon the signals produced by the exposure to the x-ray beam and corrected on the basis of signals produced by said exposure to the x-ray beam obstructed by said bone-like calibration material.

11. The bone densitometer of claim 10 wherein the signal processing means is responsive to data based upon x-rays passing through regions having only flesh to produce the correction.

12. The bone densitometer of claim 10 wherein the exposure is limited to an area within the outer dimensions of the patient.

13. The bone densitometer of claim 10 adapted to produce and process signals based upon passage of x-rays of respectively different energies through the patient.

14. The base densitometer of claim 13 wherein said power supply is constructed to apply alternate high and low voltage levels to said x-ray tube to produce said x-rays of different energies.

15. The bone densitometer of claim 14 wherein said x-ray beam is scanned across the patient and a control means for controlling the frequency of alternating said voltage is dependent upon the speed at which said beam is driven in scan motion and the beam width of said beam such that said control means applies alternating high and low voltage levels to the x-ray tube at a frequency sufficiently high that at least one of the high and low level exposures occurs during the short time period during which the beam traverses a distance equal to about one beam thickness.

16. The bone densitometer of claim 15 in which said beam is a fan beam, and is constructed to produce pairs of high and low voltage pulses at a rate of the order of sixty per second, said fan-beam being driven along said scan at a rate of the order of one inch per second, the fan beam having thickness of between about one and three millimeters.

17. The bone densitometer of claim 14 constructed to cause said power supply to supply alternate high and low voltage to said x-ray tube and said x-ray beam passes through said bone-like calibration material for the duration of every other high and low voltage pulse pair.

18. The bone densitometer of claim 10 wherein said beam is a scanned fan beam and said detector means comprises a linear array of integrating detector elements controlled to integrate the detected signal repeatedly over time periods that are short relative to the time required to advance the x-ray scan pattern by one beam thickness.

19. The bone densitometer of claim 10 including an analog to digital converter to convert each integrated value to a digital signal and a digital computer means for producing said measurement of bone content of the patient by processing a stream of said digital signals.

20. The bone densitometer of claim 14 wherein said beam is a scanned fan beam and said x-ray beam passes through said bone-like calibration material at least twice per every four scan lines for a period during which the fan-beam moves less than about one beam thickness and wherein said detector means comprises an integrating detector controlled to integrate the detected signal repeatedly over short time periods relative to the time required to advance said x-ray tube in its scan by one beam thickness of resolution.

21. The bone densitometer of claim 20 wherein said detector means comprises a linear array of integrating detector elements.

22. The bone densitometer of claim 10 in which the bone-like calibration material is rotated on a disc that causes said beam to periodically pass through the calibration material for a period sufficiently small that the distance traversed by the beam during the interruption is not more than about one fan beam thickness.

23. The bone densitometer of claim 22 wherein said beam is a fan beam arranged with the longitudinal dimension of its cross-section arranged substantially radially with the said disc.

24. The bone densitometer of claim 23 wherein said detector means comprises a linear array of integrating detector elements controlled to integrate the detected signal repeatedly over short time periods relative to the time required to advance said x-ray tube in its scan by one fan beam thickness of resolution.

25. The bone densitometer of claim 10 wherein said signal processing means is responsive to distinguish, from the set of signals produced by the x-ray beam, a subset of signals which corresponds to regions of the patent having only flesh, and said signal processing means being responsive to signals from said subset as the basis for producing the correction.

26. The bone densitometer of claim 10 wherein said beam is a fan beam, including a fan beam collimator to form and direct a fan beam of x-rays through a part of the patient that includes regions having bone and adjacent regions having only flesh, said x-ray tube, fan beam collimator, means to move the callibration material, and detector means driven in unison so as to scan relative to said patient, over portions of the patient having bone and adjacent portions having only flesh.

27. The bone densitometer of claim 10 further comprising:
a cone beam collimator to form and direct a cone beam of x-rays through a part of the patient that includes regions having bone and adjacent regions not having bone.

28. The bone densitometer of claim 27 wherein said detector means comprises an x-ray image intensifier tube.

29. The bone densitometer of claim 27 including an analog to digital converter to convert each integrated value to a digital signal and a digital computer means for producing said measurement of bone content of the patient by processing a stream of said digital signals.

30. The bone densitometer of claim 27 in which the bone-like calibration material is rotated into the beam on a disc oriented such that said cone beam passses through the calibration material.

31. The bone densitometer of claim 27 wherein said signal processing means is responsive to distinguish, from the set of signals produced by the x-ray beam, a subset of signals which corresponds to regions of the patent having only flesh, and said signal processing means being responsive to signals from said subset as the basis for producing the correction.

32. The bone densitometer of claim 27 in which the bone-like calibration material is inserted into and removed from said beam by means for sliding the material into and out of the cone beam.

33. The bone densitometer of claim 10 including sandwich detector means responsive to different energies in the beam.

34. The bone densitometer of claim 10 including pulse height analysis means for identifying x-rays of different energies in the beam.

35. A method of measuring bone content in a patient who is held in fixed position comprising:
generating an x-ray beam;
exposing the patient by passing the x-ray beam through portions of the patient having bone and adjacent portions having only flesh;
passing the x-ray beam through a predetermined bone-like calibration material in the course of exposing the patient such that portions of the patient are exposed both to the x-ray beam and to the beam obstructed by said predetermined bone-like calibration material;
detecting x-rays attenuated by the patient, calibrating signals from detected x-rays using data based upon x-rays attenuated by said calibration material; and processing signals from detected x-rays to provide a measurement of bone content in the patient.

36. The method of claim 35 wherein every region exposed to the x-rays is exposed to both rays that are attenuated by passing through said calibration material and rays that are not attenuated to effectively form respective images.

37. The method of claim 35 or 36 conducted to effectively produce respective images of the patient based upon at least two different levels of x-ray energy.

38. The method of claim 35 wherein the signal calibrating comprises selecting data based upon x-rays attenuated by said calibration material in regions adjacent to bone.

39. The method of claim 35 further comprising restraining said x-ray tube from scanning beyond the outer dimensions of the patient.

40. An x-ray bone densitometer comprising an x-ray tube means and associated power supply which generates an x-ray beams of two different energies, means to expose to the x-ray beam regions of a patient to be analyzed, means to insert into and remove from the x-ray beam a piece of bone-like calibration material of predetermined properties such that all regions of the patient are exposed to the x-ray beams of different energies and to the beams of different energies obstructed by the bone-like calibration material, detector means arranged on the opposite side of the patient to detect x-rays and produce signals corresponding to the amount of x-rays transmitted through the patient, and signal processing means responsive to signals from the detector means to produce an indication of the content of bone within the patient based upon the signals produced by the exposure to the x-ray beams and the signals produced by the exposure to the x-ray beams obstructed by the bone-like calibration material.

* * * * *

UNITED STATES PATENT AND TRADEMARK OFFICE
CERTIFICATE OF CORRECTION

PATENT NO.   : 5,040,199

DATED        : August 13, 1991

INVENTOR(S)  : Jay A. Stein

It is certified that error appears in the above-identified patent and that said Letters Patent is hereby corrected as shown below:

Col. 6, line 68, " "A" " should be -- "$\overline{A}$" --.

Signed and Sealed this

Ninth Day of March, 1993

Attest:

STEPHEN G. KUNIN

Attesting Officer     Acting Commissioner of Patents and Trademarks